(12) United States Patent
Birnkrant (10) Patent No.: US 8,844,530 B2
(45) Date of Patent: Sep. 30, 2014

(54) COMBINATION LUNG VENTILATION AND MUCUS CLEARANCE APPARATUS AND METHOD

(75) Inventor: David J. Birnkrant, Moreland Hills, OH (US)

(73) Assignee: Hill-Rom Services Pte. Ltd., Singapore (SG)

( * ) Notice: Subject to any disclaimer, the term of this patent is extended or adjusted under 35 U.S.C. 154(b) by 398 days.

(21) Appl. No.: 12/620,088

(22) Filed: Nov. 17, 2009

(65) Prior Publication Data

US 2010/0122699 A1    May 20, 2010

Related U.S. Application Data

(60) Provisional application No. 61/115,176, filed on Nov. 17, 2008.

(51) Int. Cl.

| A62B 18/02 | (2006.01) |
|---|---|
| A62B 9/02 | (2006.01) |
| A61M 16/00 | (2006.01) |
| A61M 16/04 | (2006.01) |
| A61M 16/10 | (2006.01) |
| A61M 16/08 | (2006.01) |
| A61M 1/00 | (2006.01) |
| A61M 16/06 | (2006.01) |

(52) U.S. Cl.
CPC .............. *A61M 16/10* (2013.01); *A61M 16/06* (2013.01); *A61M 16/0493* (2013.01); *A61M 16/0006* (2013.01); *A61M 16/0009* (2013.01); *A61M 16/0683* (2013.01); *A61M 16/0808* (2013.01); *A61M 2210/0625* (2013.01); *A61M 2210/0618* (2013.01); *A61M 1/0023* (2013.01)
USPC ............ 128/205.19; 128/205.24; 128/205.25; 128/206.22; 128/204.21; 128/206.28

(58) Field of Classification Search
CPC ............. A61M 2210/0618; A61M 2210/0625; A61M 16/0493; A61M 16/0023; A61M 16/10; A61M 16/06; A61M 16/0683; A61M 16/0009; A61M 16/0808; A61M 16/0006
USPC ............ 128/204.18, 204.21, 205.12, 205.19, 128/205.25, 206.21, 206.27–206.29, 128/207.13–207.14, 206.22, 128/206.27–206.29, 207.13–207.14, 128/205.24; 604/317, 540, 319, 320

See application file for complete search history.

(56) References Cited

U.S. PATENT DOCUMENTS

| 196,206 | A | 10/1877 | Emery |
|---|---|---|---|
| 1,044,031 | A | 11/1912 | Drager |

(Continued)

FOREIGN PATENT DOCUMENTS

| CA | 2230622 | 9/1998 |
|---|---|---|
| CN | 2 360 074 Y | 1/2000 |

(Continued)

OTHER PUBLICATIONS

International Search Report and Written Opinion from PCT/US07/81869 dated Nov. 13, 2008.

(Continued)

*Primary Examiner* — Bhisma Mehta
*Assistant Examiner* — Douglas Sul
(74) *Attorney, Agent, or Firm* — Barnes & Thornburg LLP (57) ABSTRACT

A medical device and method for combination lung ventilation and mucus clearance of a patient is disclosed. The medical device may be configured to provide lung ventilation with intermittent, on-demand mucus clearance, freeing the patient's mouth for activities of daily living such as when the patient is awake; and, in another configuration, the device can provide lung ventilation with automated mucus clearance, such as when the patient is sedated or asleep. The medical device may comprise a pressure generation source, a ventilation portion, and a mucus clearance portion. The mucus clearance portion may be separable from or separate from the ventilation portion such that the medical device is capable of maintaining lung ventilation with the mouth interface removed from the patient.

40 Claims, 5 Drawing Sheets

(56) References Cited

U.S. PATENT DOCUMENTS

| | | | |
|---|---|---|---|
| 1,343,486 A | 6/1920 | Stolle | |
| 1,358,893 A | 11/1920 | Stolle | |
| 1,959,572 A * | 5/1934 | Craig | 379/447 |
| 2,625,155 A | 1/1953 | Engelder | |
| 2,914,064 A | 11/1959 | Sandelowsky | |
| 3,342,177 A | 9/1967 | Clementz | |
| 3,426,794 A | 2/1969 | Freytag | |
| 3,682,166 A | 8/1972 | Jacobs | |
| 3,766,914 A | 10/1973 | Jacobs | |
| 4,193,406 A | 3/1980 | Jinotti | |
| 4,273,126 A | 6/1981 | Grane et al. | |
| 4,457,305 A * | 7/1984 | Shanks et al. | 128/205.12 |
| 5,109,839 A | 5/1992 | Blasdell et al. | |
| 5,211,171 A | 5/1993 | Choromokos | |
| 5,311,862 A | 5/1994 | Blasdell et al. | |
| 5,345,930 A | 9/1994 | Cardinal et al. | |
| 5,419,317 A | 5/1995 | Blasdell et al. | |
| 5,533,506 A | 7/1996 | Wood | |
| 5,542,929 A | 8/1996 | Laabs et al. | |
| 5,596,983 A * | 1/1997 | Zander et al. | 128/204.18 |
| 5,741,237 A * | 4/1998 | Walker | 604/317 |
| 5,791,340 A | 8/1998 | Schleufe et al. | |
| 5,850,835 A | 12/1998 | Takaki et al. | |
| 6,176,235 B1 | 1/2001 | Benarrouch et al. | |
| 6,209,540 B1 | 4/2001 | Sugiura et al. | |
| 6,427,691 B1 | 8/2002 | Jinotti | |
| 6,543,446 B1 | 4/2003 | Christopher | |
| 6,637,434 B2 | 10/2003 | Noble | |
| 6,652,481 B1 | 11/2003 | Brown | |
| 6,679,257 B1 | 1/2004 | Robertson et al. | |
| 6,789,538 B2 | 9/2004 | Wright et al. | |
| 6,789,540 B1 * | 9/2004 | Lin | 128/205.19 |
| 6,820,617 B2 | 11/2004 | Robertson et al. | |
| 6,860,265 B1 | 3/2005 | Emerson | |
| 6,860,270 B2 * | 3/2005 | Sniadach | 128/207.14 |
| 6,929,007 B2 | 8/2005 | Emerson | |
| 6,997,186 B2 | 2/2006 | Robertson et al. | |
| 7,032,596 B2 | 4/2006 | Thompson et al. | |
| 7,096,866 B2 | 8/2006 | Be'eri et al. | |
| 7,124,755 B2 * | 10/2006 | Van Hooser | 128/845 |
| 7,219,670 B2 | 5/2007 | Jones, Jr. et al. | |
| 7,222,623 B2 * | 5/2007 | DeVries et al. | 128/204.18 |
| D597,659 S | 8/2009 | Chandran et al. | |
| 7,594,508 B2 * | 9/2009 | Doyle | 128/204.18 |
| 7,918,222 B2 * | 4/2011 | Chen | 128/200.24 |
| 2003/0024533 A1 | 2/2003 | Sniadach | |
| 2003/0051731 A1 | 3/2003 | Be'eri et al. | |
| 2003/0075182 A1 | 4/2003 | Heidemann et al. | |
| 2003/0154980 A1 | 8/2003 | Berthon-Jones et al. | |
| 2005/0056282 A1 * | 3/2005 | Robertson et al. | 128/204.18 |
| 2005/0076913 A1 * | 4/2005 | Ho et al. | 128/206.27 |
| 2005/0139220 A1 | 6/2005 | Christopher | |
| 2005/0217675 A1 | 10/2005 | Thompson et al. | |
| 2005/0263157 A1 | 12/2005 | Olsen | |
| 2006/0084931 A1 | 4/2006 | Huang | |
| 2006/0096596 A1 | 5/2006 | Occhialini et al. | |
| 2006/0124131 A1 | 6/2006 | Chandran et al. | |
| 2006/0130845 A1 | 6/2006 | Schegerin | |
| 2006/0249158 A1 | 11/2006 | Dhuper et al. | |
| 2007/0017522 A1 | 1/2007 | Be'eri et al. | |
| 2007/0017523 A1 | 1/2007 | Be'eri et al. | |
| 2007/0089740 A1 | 4/2007 | Baumert et al. | |
| 2007/0089749 A1 * | 4/2007 | Ho et al. | 128/207.18 |
| 2007/0186928 A1 | 8/2007 | Be'eri et al. | |
| 2007/0199566 A1 | 8/2007 | Be'eri et al. | |
| 2007/0272247 A1 | 11/2007 | Porat | |
| 2007/0272248 A1 | 11/2007 | Lin | |
| 2007/0272249 A1 | 11/2007 | Chandran et al. | |
| 2008/0092895 A1 | 4/2008 | Birnkrant | |
| 2008/0142014 A1 * | 6/2008 | Jiang | 128/206.24 |
| 2009/0159084 A1 | 6/2009 | Sher et al. | |
| 2009/0173343 A1 | 7/2009 | Omura et al. | |

FOREIGN PATENT DOCUMENTS

| | | |
|---|---|---|
| GB | 23021 | 0/1914 |
| JP | 5096007 | 4/1993 |
| JP | 10165505 | 6/1998 |
| JP | 2000-51357 | 2/2000 |
| JP | 3069362 | 3/2000 |
| JP | 2004-283329 | 10/2004 |
| JP | 2006-130320 | 5/2006 |
| NZ | 223225 | 4/1990 |
| WO | 97/00092 A1 | 1/1997 |
| WO | 2004/108199 | 12/2004 |
| WO | 2006/102707 A1 | 10/2006 |
| WO | 2007/054829 | 5/2007 |
| WO | WO 2007/050557 A2 | 5/2007 |
| WO | WO 2007/114492 | 10/2007 |
| WO | 2008/051816 | 5/2008 |

OTHER PUBLICATIONS

Communication from European Application No. 07844434.6 dated Aug. 27, 2009.

Response for European Application No. 07844434.6 dated Mar. 3, 2010.

Birnkrant et al., "Noninvasive Ventilation During Gastrostomy Tube Placement in Patients with Severe Duchenne Muscular Dystropy", Pediatric Pulmonology, 41, pp. 118-193, dated Feb. 2006.

Birnkrant et al., "Use of Laryngeal Mask Airway in Patients with Severe Muscular Dystrophy who Require Sedation or Anesthesia", Pediatric Pulmonology 41, pp. 1007-1081, published Nov. 2006.

Caramez et al., "Open Lung Approach (OLA) Using Conventional Mechanical Ventilation (CMV) or High Frequency Oscillation (HFO) Improves Oxygenation and Compliance in Ards Better than the Ardsnet Protocol", Abstract, Published Nov. 2006, Respiratory Care, vol. 51, No. 11, presented at Dec. 2006 Convention.

Four pages, Pediatric Advanced Life Support Textbook from the American Heart Association including pp. 4-10 and 4-11, dated 1994.

Four page web printout from http://www.ambu.com/RespiratoryCare/Respiratory_Care.aspx? GID=GROUP51&Product . . . , date unknown, printed on Jan. 30, 2009, Ambu Mark IV—Reusable Resuscitator.

One page printout from http://www.laerdaltraining.com/lsr/, Laerdal, date unknown, printed Apr. 16, 2009.

International Search Report and Written Opinion from PCT/US09/64746 dated Jan. 20, 2010.

Printout from http://www.nagelnetwork.com/mouth.htm, 4 pgs., Mouthpieces, Flow Sensors, & Noseclips, printed Nov. 11, 2009.

Office Action for Japanese Patent Application No. 2011-536591 dated Aug. 20, 2013 5 pages) (English Translation 6 pages).

Supplemental European Search Report from related EP 09 82 6959 dated Jun. 23, 2014, 9 pages.

* cited by examiner

COMBINATION LUNG VENTILATION AND MUCUS CLEARANCE APPARATUS AND METHOD

CROSS REFERENCE TO RELATED APPLICATION

The present application claims priority to, and any other benefit of, U.S. Provisional Patent Application Ser. No. 61/115,176, filed Nov. 17, 2008, and entitled COMBINATION LUNG VENTILATION AND MUCUS CLEARANCE APPARATUS AND METHOD, the entire contents of which are hereby incorporated by reference.

FIELD OF THE INVENTION

The present application relates generally to a medical device and method for ventilation and mucus clearance of a patient. More specifically, the present application relates to a combination lung ventilation and mucus clearance device and method.

BACKGROUND

Commercially available mucus clearance devices do not provide lung ventilation. Applicant has appreciated that this is very problematic for patients who require both assisted breathing and assisted coughing, for example patients with respiratory muscle weakness who develop retained bronchial secretions due to illness or aspiration. With currently available equipment, such patients must be removed from the ventilator and connected to a separate mucus clearance device in order to remove retained respiratory secretions. This process, which requires the assistance of caregivers and active patient cooperation, can be dangerous for medically fragile patients.

SUMMARY OF THE INVENTION

The medical device of the present application utilizes the patient's mouth to provide mechanically assisted mucus clearance without interruption of mechanically assisted ventilation, which is provided via the patient's nose. The provision of positive pressure lung ventilation via the nose and negative pressure mucus clearance via the mouth greatly improves patient comfort, device efficacy and compliance. The device utilizes completely separate lung ventilation and mucus clearance circuits, avoiding bacterial contamination of the ventilation circuit and greatly reducing the risk of iatrogenically induced lung infection imposed by fluidly communicating patient interfaces and circuits. The device may be used by medically fragile patients and patients of almost any age.

The medical device of the present application also utilizes patient interfaces and flexibility in the configuration of the device's components to greatly improve efficacy, safety, comfort, compliance and patient quality of life. For example, one embodiment is configured with the positive pressure lung ventilation nose interface separate from the negative pressure mucus clearance mouth interface. With this configuration, when the patient is awake, the separate mouth interface can be removed to free the patient's mouth for activities of daily living, like speech and swallowing (with or without nasally assisted lung ventilation). In this configuration, the mouth interface is designed to be easily grasped by the patient and properly positioned by the patient when mechanically assisted coughing is necessary, without interruption of nasally assisted lung ventilation. The mouthpiece is designed so that it may be kept in place by medically fragile patients and the mouthpiece is designed to form an airtight seal even in patients with weak facial muscles.

In another embodiment, the positive pressure lung ventilation nose interface is physically coupled to the negative pressure mucus clearance mouth interface. This configuration is especially helpful when the patient is sedated, sleeping, or otherwise uncooperative, as the device can be configured to deliver mucus clearance and ventilation automatically, optimizing sleep quality and patient independence, and minimizing the risk of mucus plugging. In this configuration, a nasal-oral interface allows the patient to be ventilated and his or her airways to be cleared of respiratory secretions automatically, without caregiver assistance, permitting the patient to enjoy uninterrupted sleep, and minimizing the risk of potentially life threatening mucus plugging or aspirations when the patient is asleep and potentially unobserved by his or her caregivers.

Through these and other exemplary configurations of the medical device, medically fragile patients can maximize their ability to partake in the activities of daily living, minimize their reliance on caregivers, minimize the risk of potentially life-threatening aspiration or mucus plugging of their airways, and minimize the risk of iatrogenic respiratory infection or pneumonia. Further, the provision of combination positive pressure lung ventilation and negative pressure mucus clearance or assisted coughing in a single device decreases the size and cost of the device and improves the safety, tolerability, portability and reliability of the device when compared with designs that utilize separate positive and negative pressure devices. The complete separation of the lung ventilation and mucus clearance circuits and the specific choice of the nasal route for positive pressure lung ventilation and the oral route for negative pressure mucus clearance greatly improves flexibility of the possible device configurations and maximizes the tolerability, comfort and efficacy of the combination device.

Further aspects and concepts will become apparent to those skilled in the art after considering the following description and appended claims in conjunction with the accompanying drawings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of the invention.

DETAILED DESCRIPTION

The present application discloses a medical device and method for combination lung ventilation and mucus clearance of a patient. The medical device has a variety of uses. For example, the medical device may be used in the home for chronic care of patients with respiratory insufficiency. The device may also be used in acute care hospitals for patients requiring assistance with ventilation and/or cough, e.g., during respiratory illnesses, after surgeries, in the intensive care unit or emergency department, in the post-anesthetic recovery unit, etc. Further, the device may be used in chronic care facilities for patients with chronic impairment of breathing and cough. Portable embodiments of the medical device may be used by patients who desire mobility (e.g., attached to a wheelchair) or in the field by emergency services personnel. The device may also be used as a standalone noninvasive ventilator or as a standalone mucus clearance device. Other uses of the medical device are envisioned and are intended to be covered within the scope of the present application.

The medical device of the present application generally comprises a pressure generation source, a positive pressure lung ventilation portion, and a negative pressure mucus clearance portion and cycles between providing the patient with positive pressure lung ventilation and negative pressure mucus clearance. The single pressure generation source provides both positive pressure gas flow for lung ventilation and negative pressure suction for mucus clearance. The pressure generation source may comprise at least one outlet for the positive pressure gas flow and at least one inlet for the negative pressure suction. The ventilation portion of the medical device generally comprises an airtight nasal interface and a positive pressure flow channel or circuit having a first end and a second end. The first end of the flow channel may be in fluid communication with the outlet of the pressure generation source and the second end of the flow channel may be in fluid communication with the nasal interface.

The negative pressure mucus clearance portion of the medical device generally comprises an airtight mouth interface and a negative pressure suction channel or circuit having a first end and a second end. The first end of the suction channel may be in fluid communication with the inlet of the pressure generation source and the second end of the suction channel may be in fluid communication with the mouth interface. The negative pressure mucus clearance portion may be separable from or separate from the positive pressure ventilation portion such that the medical device is capable of maintaining lung ventilation with the mouth interface of the mucus clearance portion removed from the patient.

The medical device of the present application may provide negative pressure mucus clearance of the patient without removal of the positive pressure lung ventilation portion from the patient. The medical device may also provide positive pressure lung ventilation and negative pressure mucus clearance of the patient sequentially or concurrently without removal of either of the ventilation portion or the mucus clearance portion from the patient. A first configuration of the medical device may permit the patient to engage in daily activities like speech and swallowing, e.g., while the patient is awake. A second configuration of the medical device may provide continuous lung ventilation and automated mucus clearance, e.g., while the patient is asleep.

Figure 1:
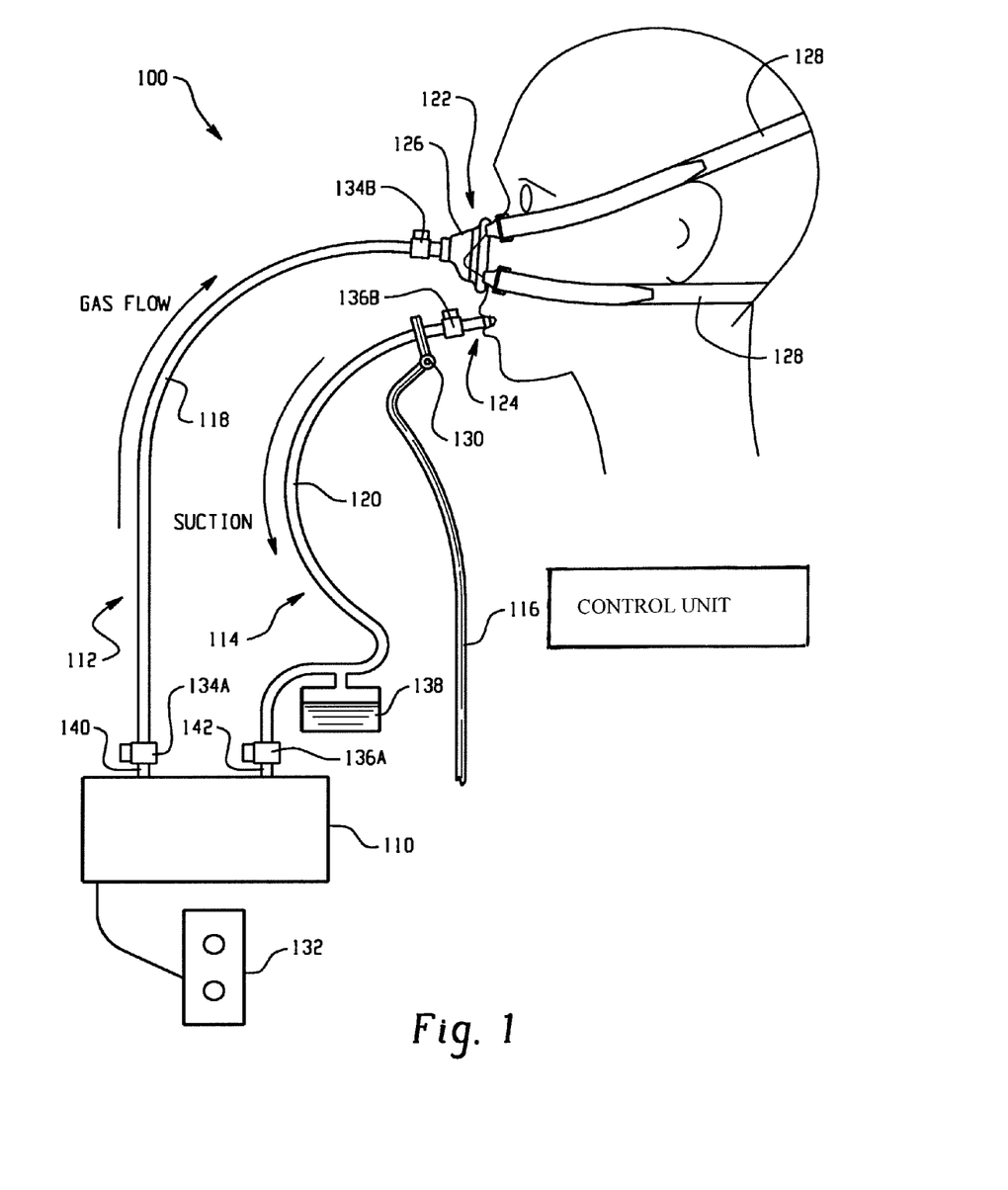
FIG. 1 illustrates a medical device for lung ventilation and mucus clearance of a patient according to an embodiment of the invention.

FIG. 1 illustrates an exemplary embodiment of a medical device 100 for combination lung ventilation and mucus clearance of a patient, with separately removable ventilation and mucus clearance interfaces. The medical device 100 includes a pressure generation source 110, a positive pressure ventilation portion 112, and a negative pressure mucus clearance portion 114, and an optional handle or bracket 116. The positive pressure ventilation portion 112 is removably connected to an outlet 140 of the pressure generation source 110 and the negative pressure mucus clearance portion 114 is removably connected to an inlet 142 of the pressure generation source.

The exemplary medical device 100 shown in FIG. 1 is configured such that the patient's mouth can be free for activities of daily living while the patient is awake and the mucus clearance portion 114 is removed from the patient, e.g., when assisted coughing is unnecessary. The mouthpiece 124 of the negative pressure mucus clearance portion 114 can easily be grasped by the patient and inserted into the mouth whenever assisted coughing is necessary and then removed from the mouth to engage in activities of daily life (e.g., speech and swallowing). Separate positive pressure ventilation and negative pressure mucus clearance circuits having separate interfaces via the nose and mouth, respectively, permit the patient's mouth to be free during assisted ventilation when assisted coughing is unnecessary. Further, separate positive pressure ventilation and negative pressure mucus clearance circuits prevent fluid communication between the circuits, avoiding bacterial cross-contamination. Separate ventilation and mucus clearance circuits also permit nasally assisted ventilation and orally assisted mucus clearance without active patient cooperation, e.g., when the patient is asleep; if the patient is sedated or unconscious; or any time the patient cannot voluntarily open his or her mouth to allow application of negative pressure to suction secretions out of his or her airways.

The pressure generation source 110 of the medical device 100 provides positive pressure gas flow for lung ventilation and negative pressure suction for mucus clearance. The positive pressure gas flow is generally provided to the patient via the outlet 140 of the pressure generation source 110. The amount of positive pressure gas flow may be adjustable and may be controlled automatically (e.g., by a control unit) or manually. For example, the pressure and flow characteristics of the positive pressure gas flow may be adapted or adjusted, either automatically or manually, to an individual patient's needs. Further, the positive pressure gas flow may be initiated by a variety of methods, e.g., by a remote control or switch 132, a patient produced flow of air into a nasal interface 122, etc. The positive pressure gas flow may be provided by a ventilation or positive pressure source configured to provide breathable air to the patient. The breathable air may be a mixture of oxygen and air. The breathable air may be provided via a pneumatic system or turbopump and may be controlled by a control unit, such as a pre-programmed processor.

The negative pressure suction is generally provided to the patient via the inlet 142 of the pressure generation source 110. The amount of negative pressure suction may be adjustable and may be controlled automatically (e.g., by a control unit) or manually. For example, the pressure and flow characteristics of the negative pressure suction may be adapted or adjusted, either automatically or manually, to an individual patient's needs. Further, the negative pressure suction may be initiated by a variety of methods by a number of different patient input devices in fluid or electrical circuit communication with the source 110, e.g., by a remote control or switch 132, a bite switch (not shown) in a mouth interface 124 activated by the patient biting and/or manipulating a portion of the mouth interface, a switch activated by the patient blinking and/or fluttering their eyes, a patient produced flow of air into the mouth interface, or intermittently using an adjustable timer, etc. The negative pressure suction may be provided by a suction or negative pressure source, e.g., a suction pump having a pressure sensing device to control operation, configured to provide adjustable negative pressure to the patient to remove respiratory secretions from the patient's airways. The suction source may be controlled by a control unit, such as a pre-programmed processor.

In the exemplary embodiment shown in FIG. 1, the positive pressure lung ventilation portion 112 of the medical device 100 comprises a flow channel or circuit 118 having a first end and a second end. The first end of the flow channel 118 is in airtight fluid communication with the outlet 140 of the pressure generation source 110 and the second end of the flow channel 118 is in airtight fluid communication with the nasal interface 122. The flow channel 118 may be made from any flexible material suitable for transferring a breathable gas to a patient, e.g., plastic tubing. The first and second end of the flow channel 118 may be connected to the outlet 140 of the pressure generation source 110 and the nasal interface 122, respectively, by any suitable means that prohibits leakage of the breathable gas, e.g., a friction fit, a threaded connector, a plug in connector, or the like. The flow channel 118 may be removable from either the outlet 140 or the nasal interface 122.

In the exemplary embodiment shown in FIG. 1, the nasal interface 122 comprises a nasal mask 126 and adjustable straps 128 securing the nasal mask in place on the patient's face. The nasal mask 126 is configured to form an airtight seal around the patient's nose and nasal passage to prohibit leakage of the positive pressure gas flow from the pressure generation source 110. As shown, the nasal interface 122 allows the patient to utilize his mouth during ventilation. In other embodiments, the nasal interface comprises a set of nasal prongs connected to the flow channel. Valves 134A, 134B in the flow channel 118 of the ventilation portion 112 may be used to control the flow of the positive pressure gas from the pressure generation source 110. One or more of the valves 134A, 134B may be located at various locations in the ventilation circuit, e.g., at the first end and the second end of the flow channel 118, within the pressure generation source 110, etc. The valves may be any suitable valve capable of controlling the flow of the positive pressure gas and may be operated automatically (e.g., by the control unit) or manually.

In the exemplary embodiment shown in FIG. 1, the negative pressure mucus clearance portion 114 of the medical device 100 comprises a suction channel or circuit 120 having a first end and a second end. The first end of the suction channel 120 is in airtight fluid communication with the inlet 142 of the pressure generation source 110 and the second end of the suction channel 120 is in airtight fluid communication with the mouth interface 124. The suction channel 120 may be made from any flexible material suitable for providing a negative pressure suction to a patient and transferring respiratory secretions, e.g., plastic tubing. The first and second end of the suction channel 120 may be connected to the inlet 142 of the pressure generation source 110 and the mouth interface 124, respectively, by any suitable means that prohibits leakage of the respiratory secretions, e.g., a friction fit, a threaded connector, a plug in connector, or the like. The suction channel 120 may be removable from either the inlet 142 or the mouth interface 124. Valves 136A, 136B in the suction channel 120 of the mucus clearance portion 114 may be used to control the negative pressure suction created by the pressure generation source 110. Valves 136A, 136B may be used to close the suction channel 120 and prevent leakage of the breathable gas via the mouth during positive pressure ventilation via the nose. One or more of the valves 136A, 136B may be located at various locations in the mucus clearance portion of the device, e.g., at the first end and the second end of the suction channel 120, within the pressure generation source 110, etc. The valves may be any suitable valve capable of controlling the negative pressure suction and may be operated automatically (e.g., by the control unit) or manually.

Figure 2A:
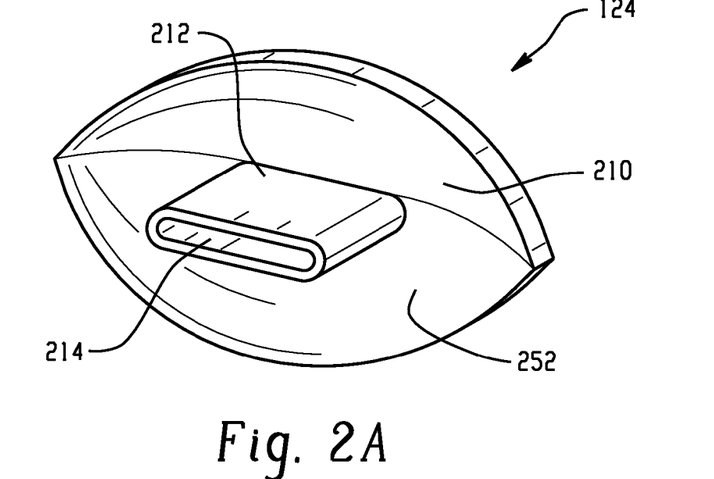
FIGS. 2A-2B illustrate a rear perspective view and a top view respectively of a mouth interface according to an embodiment of the invention.
Figure 2B:
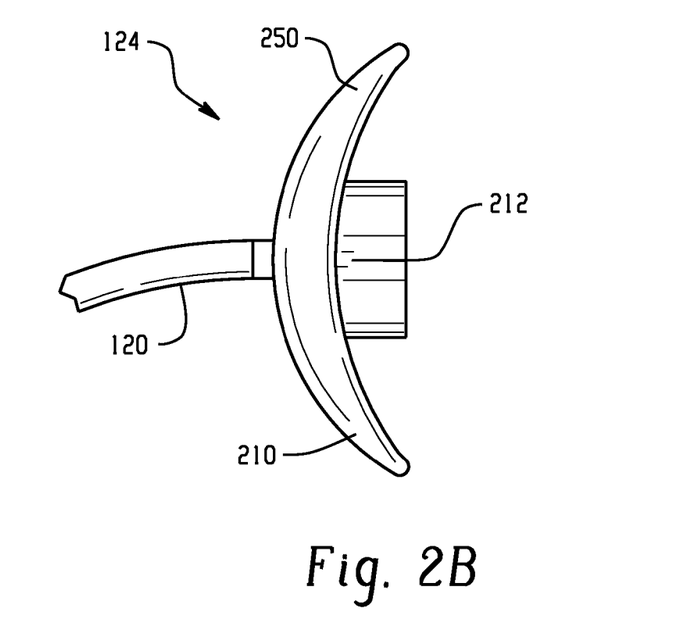

Referring now to FIGS. 2A-2B, an exemplary mouthpiece or mouth interface 124 of the medical device 100 is shown. The exemplary mouth interface 124 shown comprises a soft outer portion 210 and a hard inner portion 212 having an opening 214. The mouth interface 124 is configured for repeatable insertion and removal from the patient's mouth. The inner portion 212 is formed from one or more materials that are rigid enough to keep the opening 214 open and the conduit between the opening 214 and the suction channel 120 open during use. The hard inner portion 212 of the mouth interface 124 extends past the teeth, passes on top of the patient's tongue, and ends with the opening 214 in the patient's oral cavity (i.e., the mouth cavity including the front of the tongue) or oropharynx (i.e., the last third of the tongue). As such, the patient does not need to open his or her mouth to achieve mucus clearance because the oropharyngeal mouth interface 124 is in fluid communication with the patient's airway during use.

In the exemplary embodiment shown in FIGS. 2A-2B, the soft outer portion 210 of the mouth interface 124 is configured to rest between the inside of the patient's lips and the outer surface of the patient's gums and teeth to form an airtight seal with the patient's mouth and permitting communication of negative suction pressure to the patient's airway. In the exemplary embodiment shown, the outer portion 210 is curved and shaped similar to a portion of an orange wedge or some sports mouth guards. An outer surface 250 that is positioned against the inner surface of the lips is convex and an inner surface 252 that is positioned against the outer surface of the gums and teeth is concave to form an airtight seal at the mouth. The outer portion 210 may be made from a material capable of being inserted in a patient's mouth, e.g., foam, soft plastic, soft rubber, or the like. In the exemplary mouth interface 124 shown, the outer portion 210 is made of a soft material such that the mouth interface may be kept in place by medically fragile patients with weak facial muscles and used by patients of about any age. The soft material conforms to the anatomy of the mouth to form an airtight seal and also prevents damages to the lips, gums, and teeth of the patient. The outer portion 210 may be provided in various sizes and a particular size selected based on the size of the patient's mouth and the patient's individual needs.

In the exemplary embodiment shown in FIGS. 2A-2B, the hard inner portion 212 of the mouth interface 124 is held between the patient's teeth and is configured to extend past the teeth, passing on top of the tongue, and with the opening 214 positioned in the oral cavity or oropharynx of the patient such that the patient's airway can be accessed for removal of the respiratory secretions, e.g., the inner portion may extend about 1 to 7 cm past the teeth or about 1 to 7 cm past the inner surface 252 of the outer portion 210 of the mouth interface. The opening 214 in the inner portion 212 is in fluid communication with the suction channel 120 and configured such that the respiratory secretions can be removed from the airway of the patient. In the exemplary mouth interface 124 shown, the inner portion 212 and the opening 214 are generally oval, although other shapes and configurations may be used, e.g., circular, elliptical, rectangular, square, etc. The inner portion 212 may be made from a material capable of being held between the patient's teeth, e.g., plastic, hard rubber, or the like. In the exemplary mouth interface 124, the inner portion 212 is made from a material of sufficient rigidity such that it may be held between the patient's teeth without collapsing and sufficient rigidity that the conduit between opening 214 and channel 120 will not collapse during use.

Further, the outer portion 210 and the inner portion 212 may be a unitary construction. The mouth interface 124 may also comprise an adjustable strap (not shown) such that the mouth interface is held within the patient's mouth.

Other configurations of a mouth interface that is inserted into the mouth of the patient are envisioned. For example, the mouth interface may comprise a soft mouthpiece of unitary construction having an opening. The mouthpiece (not shown) may be wedge-shaped, e.g., similar to a wedge of a globe or cylinder. In this embodiment, an end of the wedge-shaped mouthpiece having an opening is inserted into the patient's mouth with a thicker portion of the wedge at least partially between the patient's teeth/gums and a thinner portion of the wedge with the opening extending into the oral cavity or oropharynx of the patient. The opening extends through the mouthpiece and is in fluid communication with the suction channel 120 and the patient's airway during use such that the respiratory secretions can be removed from the airway of the patient. The patient closes his or her lips around the wedge to sufficiently seal the airway.

Referring again to FIG. 1, a receptacle 138 is shown in the mucus clearance circuit. The receptacle 138 collects the respiratory secretions suctioned from the patient's airways. The negative pressure suction pulls the secretions from the patient's airways, through the suction channel 120, and into the receptacle 138. The receptacle 138 may be removable from the mucus clearance circuit and may comprise a fluid height detector to automatically shut off the suction if the receptacle is full. The receptacle 138 may be located at various locations in the mucus clearance portion of the device, e.g., within the pressure generation source 110, towards the first end of the suction channel 120, at the discharge of the suction source, etc. Further, valves 136A, 136B in the suction channel 120 of the mucus clearance portion 114 may be used to control the negative pressure suction from the pressure generation source 110. One or more of the valves 136A, 136B may be located at various locations in the mucus clearance portion of the device, e.g., at the first end and the second end of the suction channel 120, within the pressure generation source 110, etc. The valves may be any suitable valve capable of controlling the negative pressure suction and may be operated automatically (e.g., by the control unit) or manually. Valves 136A, 136B, when closed, also prevent leakage of breathable gas out of the patient's mouth during positive pressure ventilation via the patient's nose.

As shown in FIG. 1, the medical device 100 may comprise an optional handle or bracket 116 removably attached to the mucus clearance portion 114 of the device. The bracket or handle 116 is configured to support the mucus clearance portion 114 and may be grasped by the patient to assist with insertion of the mouth interface 124 into the patient's mouth. The bracket or handle 116 may also be held stationary such that the patient can insert the mouth interface 124 without using his or her hands. As shown, the bracket or handle 116 has a "gooseneck" shape, although other shapes and configurations are envisioned. The "gooseneck" shape of the handle or bracket 116 provides clearance for the patient to insert the mouth interface 124. The handle or bracket 116 comprises an adjustable joint 130 for positioning of the mouth interface 124. Further, the handle or bracket 116 may comprise a switch for initiating negative pressure suction.

In some embodiments, the medical device is battery powered to permit portability of the medical device. The medical device may also be configured to humidify the air provided to the patient. The medical device may also add nebulized medications to the air provided to the patient. The medical device may also act as an intermittent positive pressure breathing device by using pressure to passively fill the lungs of the patient when a breath is initiated. A manometer and at least one valve may be used to terminate the flow of inspired air when a predetermined pressure is reached on inhalation. The medical device may also incorporate high frequency intrapulmonary percussive ventilation into one of the circuits, loosening secretions via positive pressure bursts of gas delivered at about 100-300 cycles/minute, thereby loosening respiratory secretions prior to extraction by the negative pressure mucus clearance portion of the device.

As shown in FIG. 1, the negative pressure mucus clearance portion 114 of the medical device 100 is separate from the positive pressure lung ventilation portion 112 such that the medical device is capable of maintaining lung ventilation via the nasal interface 122 with the mouth interface 124 removed from the patient. Further, in this configuration, the medical device 100 provides negative pressure mucus clearance of the patient on demand, by inserting the mouth interface 124 into the patient as needed, without removal of the positive pressure ventilation portion 112 from the patient. The mouth interface 124 can be removed from the patient when mucus clearance is no longer needed, so that the patient's mouth is free to engage in activities of daily living, e.g., speech and swallowing. The medical device 100 may thus provide lung ventilation and mucus clearance of the patient sequentially or concurrently and pursuant to a schedule controlled by the patient and/or his caregiver. This flexibility of device configuration maximizes patient independence and device comfort, efficacy and compliance. The mouth interface 124 is designed to be easily removed by the patient such that his or her mouth is free for drinking, eating, and speech when mechanically assisted coughing or mucus extraction is unnecessary; and is easily replaced by the patient or his caregiver, when negative pressure mucus clearance is necessary. This embodiment of the device may be preferred during the day, when the patient is awake and desires the greatest number of care options.

Further, complete fluid separation of the negative pressure mucus clearance portion 114 and the positive pressure ventilation portion 112 of the medical device 100 permits patients to customize the availability of mucus clearance therapy. For example, patients who are weaker can have the mouthpiece immediately available to them via the handle or bracket 116. The handle or bracket 116 can be placed in a position near the patient that allows the patient to grasp the mouthpiece at will and without using his or her hands. Thus, a patient with progressive weakness can adjust the location of the mouthpiece to his or her own preference. Moreover, the provision of positive pressure lung ventilation exclusively via the nasal route and negative pressure mucus clearance exclusively via the oral route is designed to maximize patient comfort and device efficacy and compliance, in addition to maximizing device configurations and flexibility of use.

A method of connecting a person to the medical device 100 generally comprises positioning the nasal interface 122 in airtight fluid communication with the person's nasal passages (e.g., securing a nasal mask to the person using adjustable straps) and inserting the separate mouth interface 124 into the person's mouth to make an airtight seal. The soft outer portion 210 of the mouth interface 124 rests between the inside surface of the person's lips and the outer surface of the person's gums and teeth. The hard inner portion 212 of the mouth interface 124 extends past the person's teeth, passes on top of the person's tongue and ends in the oral cavity or oropharynx of the person. A first end of the positive pressure flow channel 118 is connected to the outlet 140 of the pressure generation source 110. A second end of the positive pressure flow channel 118 is connected to the nasal interface 122. A first end of the negative pressure suction channel 120 is connected to the inlet 142 of the pressure generation source 110. A second end of the negative pressure suction channel 120 is connected to the mouth interface 124. The positive pressure ventilation portion 112 of the device and the negative pressure mucus clearance portion 114 of the device are separate and not in fluid communication. The flow channel 118 and the suction channel 120 are separate and not in fluid communication. The nasal interface 122 and the mouth interface 124 are separate both in the sense that they are not physically connected and in the sense that they are not in fluid communication (except perhaps the theoretical possibility that some small quantity of clean gas from the ventilation portion could mix within the patient with gas removed from the patient by the mucus clearance portion) so that mucus does not flow back through the same conduit through which air is provided.

A method of using the medical device for lung ventilation and mucus clearance of a patient generally comprises providing a positive pressure flow of gas to the lungs of the patient via a first interface in fluid communication with the patient's nasal passages and a negative pressure suction to the airway of the patient via a second interface in fluid communication with the patient's mouth. The medical device is generally configured to provide positive pressure lung ventilation and negative pressure mucus clearance of the patient sequentially or concurrently. The medical device generally comprises a positive pressure lung ventilation circuit and a negative pressure mucus clearance circuit that are completely separated to prohibit fluid communication between the circuits and bacterial cross-contamination.

Referring back to FIG. 1, the exemplary medical device 100 is configured to cycle between providing positive pressure lung ventilation and negative pressure mucus clearance of the patient, either manually or automatically. In one embodiment, positive pressure lung ventilation is electronically controlled such that the pressure and flow characteristics of the positive pressure gas are adjustable. For example, the pressure and flow of the positive pressure gas may be increased or decreased in response to the patient's needs, e.g., sensing whether the patient is attempting to take a shallow or deep breath, multiple breaths, etc. During lung ventilation, the positive pressure gas is delivered to the patient via the flow channel 118 and the nasal interface 122. The valves 134A, 134B in the ventilation circuit are open to allow for flow of the positive pressure gas. Further, the valves 136A, 136B in the mucus clearance circuit are closed to prevent negative pressure suction and to prevent leakage of gas out of the patient's mouth during positive pressure ventilation via the nose.

Negative pressure suction may be initiated automatically (e.g., triggered by an adjustable timer of a control unit) or manually by the patient or caregiver (e.g., using a switch 132). When the negative pressure suction is triggered, a deep breath is delivered to the patient via the positive pressure nasal ventilation portion 112 of the medical device 100. The valves 134A, 134B in the ventilation circuit then close and the valves 136A, 136B in the negative pressure mucus clearance circuit open. Negative pressure suction is then applied to the patient via the suction channel 120 and mouth interface 124 to remove respiratory secretions from the patient's airway and deposit them in the receptacle 138. When negative pressure suction is complete, the valves 136A, 136B in the mucus clearance circuit close and the valves 134A, 134B in the positive pressure ventilation circuit open to resume nasal ventilation. This cycling between lung ventilation and mucus clearance of the patient may be repeated for a desired number of treatments.

Figure 3:
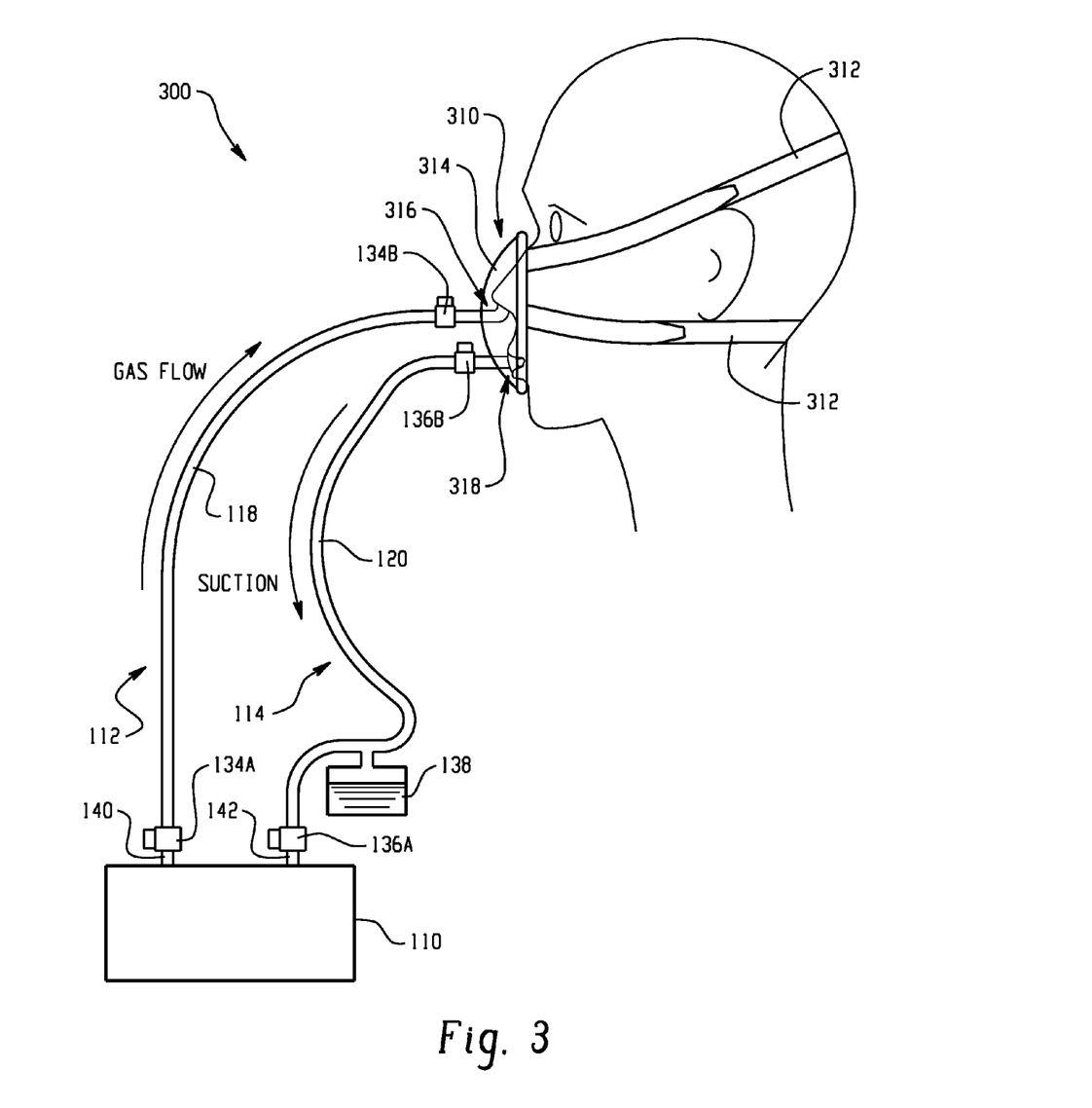
FIG. 3 illustrates a medical device according to an embodiment of the invention.

FIG. 3 illustrates an exemplary embodiment of a medical device 300 for combination lung ventilation and mucus clearance of a patient. Similar to medical device 100 of FIG. 1, the medical device 300 comprises a pressure generation source 110, a positive pressure ventilation portion 112, and a negative pressure mucus clearance portion 114. The ventilation portion 112 and the mucus clearance portion 114 are completely separated in the sense that they have no fluid communication (except perhaps the theoretical possibility that some small quantity of clean gas from the ventilation portion could mix within the patient with gas removed from the patient by the mucus clearance portion) so that mucus does not flow back through the same conduit through which air is provided, e.g., to prohibit bacterial cross-contamination. The ventilation portion 112 is removably connected to an outlet 140 of the pressure generation source 110 and the mucus clearance portion 114 is removably connected to an inlet 142 of the pressure generation source. As shown, the medical device 300 is configured to provide continuous positive pressure lung ventilation and automated negative pressure mucus clearance without patient cooperation, e.g., without interrupting the patient's sleep.

As shown in FIG. 3, the medical device 300 comprises an airtight patient interface 310. The patient interface 310 includes a nasal interface 316 separate from a mouth interface 318—separate in the sense that, although they are physically connected, they are not in fluid communication (except perhaps the theoretical possibility that some small quantity of clean gas from the ventilation portion could mix within the patient with gas removed from the patient by the mucus clearance portion) so that mucus does not flow back through the same conduit through which air is provided. This is in contrast with a simple mask that forms a plenum that contains and fluidly connects the patient's nose and mouth. As shown, the patient interface 310 is a combination nasal-oral mask 314 configured to simultaneously hold the nasal interface 316 in airtight fluid communication with the patient's nasal passages, hold the mouth interface 318 in airtight fluid communication with the patient's mouth, and keep the suction channel 120 separate from the flow channel 118 so that mucus does not flow back through the same conduit through which air is provided. The nasal interface 316 is in fluid communication with the flow channel 118 of the positive pressure ventilation portion 112 and the mouth interface 318 is in fluid communication with the suction channel 120 of the negative pressure mucus clearance portion 114. The nasal interface 316 and the mouth interface 318 may be removably attached to the nasal-oral mask 314. Further, the patient interface 310 comprises adjustable straps 312 that may be used to secure the nasal-oral mask 314 to the patient's face.

Figure 4A:
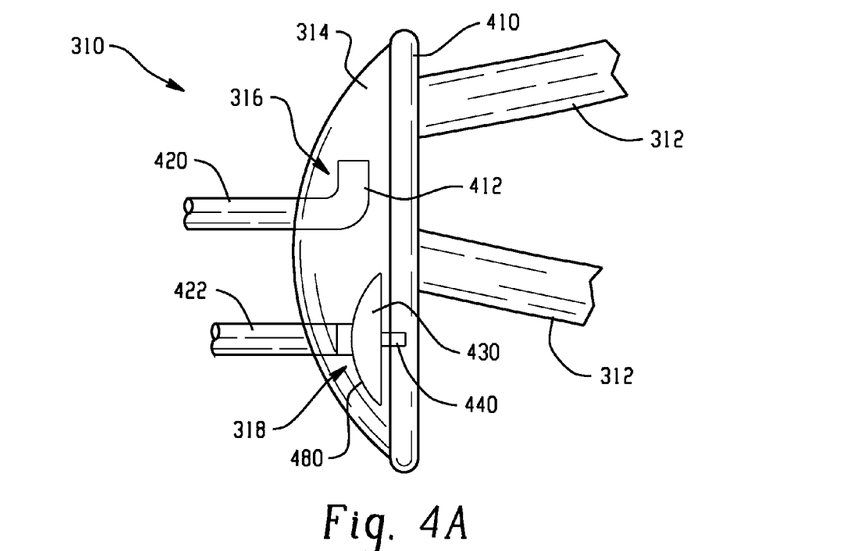
FIGS. 4A-4B illustrate a side view and a rear view respectively of a patient interface according to an embodiment of the invention.
Figure 4B:
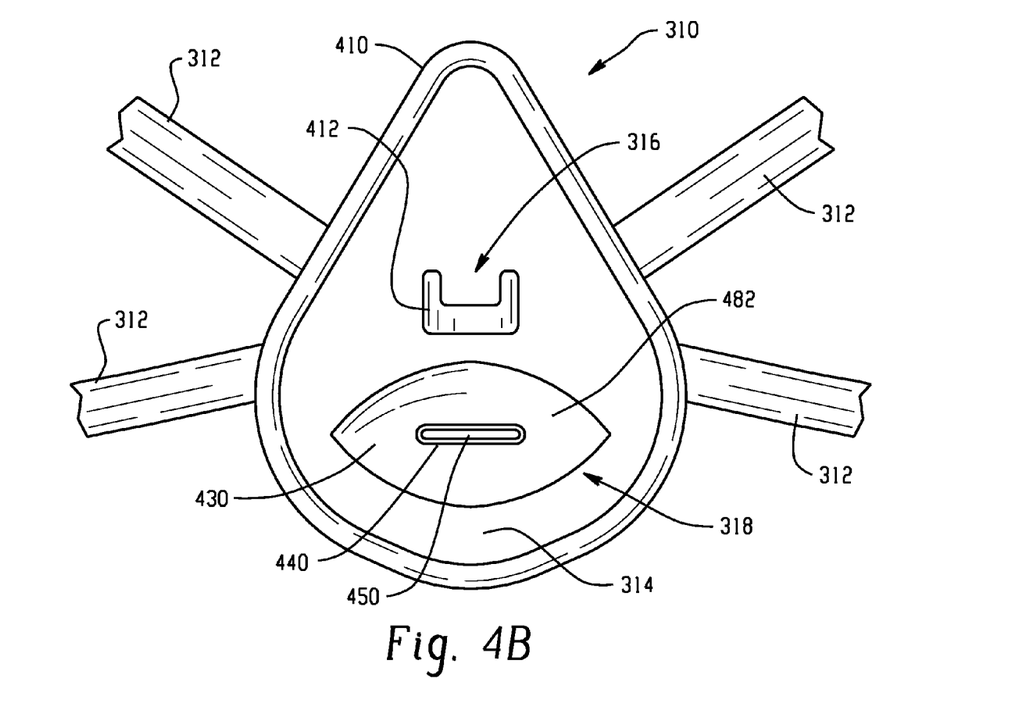

As shown in FIGS. 4A-4B, the nasal-oral mask 314 of the patient interface 310 is configured to form a seal around the patient's nose and mouth to prohibit leakage of the positive pressure gas flow from the pressure generation source 110. The nasal-oral mask 314 includes padding 410 that provides comfort to the patient and prohibits leakage of the gas flow between the mask and the patient's face. The nasal-oral mask 314 comprises an inlet 420 connected to the nasal interface 316 through which air is forced into the nose for lung ventilation and an outlet 422 connected to the mouth interface 318 through which mucus is suctioned out of the airway via the mouth. As shown, no fluid communication exists between the inlet 420 and the outlet 422. The inlet 420 is connected to the flow channel 118 of the positive pressure ventilation portion 112 of the device; the outlet 422 is connected to the suction channel 120 of the negative pressure mucus clearance portion 114 of the device.

In the exemplary embodiment shown in FIGS. 4A-4B, the nasal interface 316 of the nasal-oral mask 314 comprises a set of nasal prongs 412, although other nasal interfaces may be used, e.g, a nasal mask that makes an airtight seal with the patient's nasal passages, etc. Like the mouth interface 124 of exemplary medical device 100, the mouth interface 318 of the nasal-oral mask 314 comprises a mouthpiece comprising a soft outer portion 430 and a hard inner portion 440 having an opening 450 although perhaps other mouth interfaces might be used. The soft outer portion 430 of the mouthpiece shown is configured to rest between the inside surface of the patient's lips and the outer surface of the patient's gums and teeth to make an airtight seal with the patient's mouth and communicating airway. In the exemplary embodiment shown, the outer portion 430 is curved and shaped similar to a portion of an orange wedge or some sports mouth guards. An outer surface 480 is convex and positioned against the inside surface of the patient's lips and an inner surface 482 is concave and positioned against the outside portion of the patient's gums and teeth, thereby forming an airtight seal. The hard inner portion 440 of the mouthpiece is held between the patient's teeth and is configured to extend past the teeth, passing on top of the patient's tongue, and with the opening 450 positioned in the oral cavity or oropharynx of the patient such that the patient's airway can be accessed for removal of the respiratory secretions, e.g., the inner portion may extend about 1 to 7 cm past the teeth or about 1 to 7 cm past the inner surface 482 of the mouth interface. The opening 450 in the inner portion 440 is in fluid communication with the negative pressure suction channel 120 and configured such that the respiratory secretions can be removed from the airway of the patient. However, other configurations of a mouth interface 318 having a mouthpiece that is inserted into the mouth of the patient are envisioned. The inner portion 440 is made from a material of sufficient rigidity such that it may be held between the patient's teeth without collapsing and sufficient rigidity that the conduit between opening 450 and channel 120 will not collapse during use.

Similar to medical device 100, the negative pressure mucus clearance portion 114 of medical device 300 is separable from the positive pressure ventilation portion 112 such that the medical device is capable of maintaining positive pressure lung ventilation via the nasal interface 316 with the mouth interface 318 removed from the patient. Further, the medical device 300 may provide negative pressure mucus clearance of the patient with or without removal of the positive pressure ventilation portion 112 from the patient. The medical device 300 may also provide lung ventilation and mucus clearance of the patient sequentially or concurrently without removal of either of the positive pressure ventilation portion 112 or the negative pressure mucus clearance portion 114 from the patient.

Further, this embodiment of the device, which includes an integrated nasal-oral patient interface 310 incorporating a nasal interface 316 for positive pressure ventilation with a separate, non-communicating oral interface 318 for negative pressure mucus clearance, permits automated mucus clearance of a sleeping, sedated, or otherwise uncooperative patient. The patient does not have to open his or her mouth to achieve mucus clearance because the mouthpiece forms an airtight seal and connects the negative pressure mucus clearance portion 114 of the medical device 300 with the patient's airway. The lack of fluid communication and completely separate coupling of the nasal 316 and oral 318 interfaces and the separation of the positive pressure ventilation portion of the device 112 from the negative pressure mucus clearance portion of the device 114 prevent contaminated respiratory secretions from being forced into the patient's lungs under positive pressure, reducing the risk of lung infection.

A method of connecting a person to the medical device 300 generally comprises positioning the nasal interface 316 in fluid communication with the person's nasal passages, inserting the mouth interface 318 into the person's mouth, and securing the nasal-oral patient interface 310 to the person to simultaneously hold the nasal interface in airtight fluid communication with the person's nasal passages and the mouth interface in airtight communication with the person's mouth. The soft outer portion 430 of the mouth interface 318 is positioned between the inside surface of the person's lips and the outer surface of the person's gums and teeth. The hard inner portion 440 of the mouth interface 318 extends past the person's teeth, passes on top of the person's tongue and ends in the person's oral cavity or oropharynx. A first end of the positive pressure flow channel 118 is connected to the outlet 140 of the pressure generation source 110. A second end of the flow channel 118 is connected to the nasal interface 316 via the inlet 420. A first end of the negative pressure suction channel 120 is connected to the inlet 142 of the pressure generation source 110. A second end of the suction channel 120 is connected to the mouth interface 318 via the outlet 422. The positive pressure lung ventilation portion of the device 112 and the negative pressure mucus clearance portion of the device 114 are separate and not in fluid communication. The flow channel 118 and the suction channel 120 are separate and not in fluid communication. The nasal interface 316 and the mouth interface 318 are separately coupled and not in fluid communication (except perhaps the theoretical possibility that some small quantity of clean gas from the ventilation portion could mix within the patient with gas removed from the patient by the mucus clearance portion).

Referring again to FIG. 3, the medical device 300 is configured to cycle between providing positive pressure lung ventilation and negative pressure mucus clearance of the patient, either manually or automatically. In one embodiment, lung ventilation is electronically controlled such that the pressure and flow characteristics of the positive pressure gas are adjusted to the patient's needs. During lung ventilation, the positive pressure gas is delivered to the patient via the flow channel 118 and the nasal interface 316. The valves 134A, 134B in the ventilation circuit are open to allow for flow of the positive pressure gas. Further, the valves 136A, 136B in the mucus clearance circuit are closed to prevent negative pressure suction and to prevent leakage of gas out of the patient's mouth during positive pressure nasal ventilation.

Negative pressure suction may be initiated automatically (e.g., triggered by an adjustable timer as the patient sleeps) or manually by the patient or caregiver. In addition, an algorithm may be used to automatically trigger negative pressure suction. For example, the algorithm may be used to interpret changes in the airflow from the patient that are consistent with lower airway secretion retention or mucus plugging. When the negative pressure suction is triggered, a deep breath is delivered to the patient via the positive pressure ventilation portion 112 of the medical device 300. The valves 134A, 134B in the ventilation circuit then close and the valves 136A, 136B in the mucus clearance circuit open. Negative pressure suction is then applied to the patient via the suction channel 120 and mouth interface 318 to remove respiratory secretions from the patient's airway and deposit them in the receptacle 138. When negative pressure suction is complete, the valves 136A, 136B in the mucus clearance circuit close and the valves 134A, 134B in the ventilation circuit open to resume ventilation. This cycling between lung ventilation and mucus clearance of the patient may be repeated for a desired number of treatments, e.g., automated cycling can occur every few minutes while the patient sleeps or is sedated.

Figure 5:
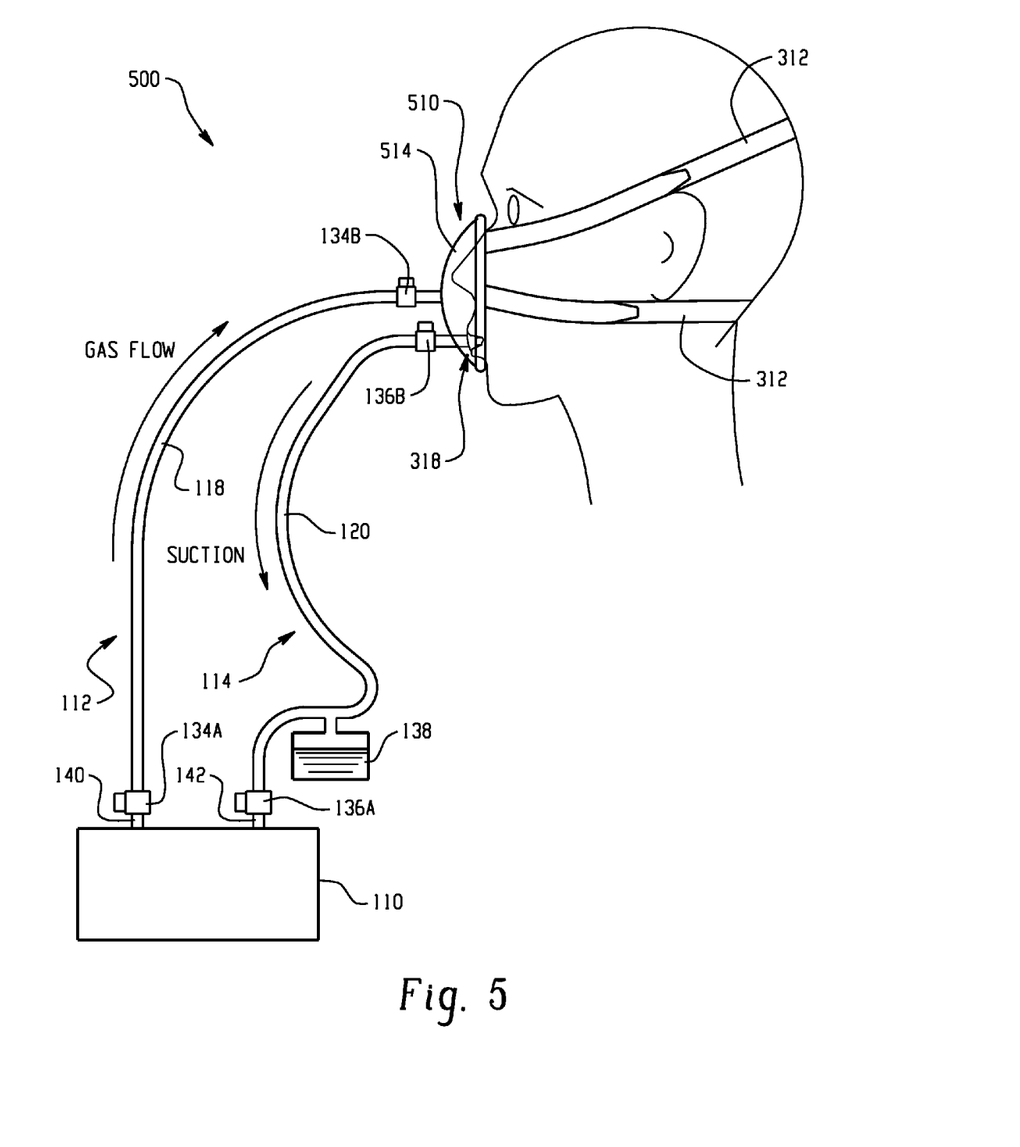
FIG. 5 illustrates a medical device according to an embodiment of the invention.

In one exemplary embodiment shown in FIG. 5, the medical device 500 comprises an airtight patient interface 510 that includes an airtight mask 514 separate from the mouth interface 318—separate in the sense that, although they are physically connected, they are not in fluid communication (except perhaps the theoretical possibility that some small quantity of clean gas from the ventilation portion could mix within the patient with gas removed from the patient by the mucus clearance portion) so that mucus does not flow back through the same conduit through which air is provided. The patient interface 510 is configured to simultaneously hold the mask 514 in airtight fluid communication with at least the patient's nasal passages, hold the mouth interface 318 in airtight fluid communication with the patient's mouth, and keep the suction channel 120 separate from the flow channel 118 so that mucus does not flow back through the same conduit through which air is provided. The mask 514 is in fluid communication with the flow channel 118 of the positive pressure ventilation portion 112 and the mouth interface 318 is in fluid communication with the suction channel 120 of the negative pressure mucus clearance portion 114. The mouth interface 318 may be removably attached to the mask 514. Further, the patient interface 510 comprises adjustable straps 312 that may be used to secure the mask 514 to the patient's face.

The mask 514 of the patient interface 510 is configured to form a seal around the patient's nose and mouth to prohibit leakage of the positive pressure gas flow from the pressure generation source 110. The mask 514 includes padding that provides comfort to the patient and prohibits leakage of the gas flow between the mask and the patient's face. The mask 514 comprises an inlet through which air is forced into the nose for lung ventilation and an outlet connected to the mouth interface 318 through which mucus is suctioned out of the airway via the mouth. As shown, no fluid communication exists between the inlet and the outlet. The inlet is connected to the flow channel 118 of the positive pressure ventilation portion 112 of the device; the outlet is connected to the suction channel 120 of the negative pressure mucus clearance portion 114 of the device.

Further, this embodiment of the device, which includes an integrated interface 510 incorporating a mask 514 for positive pressure ventilation with a separate, non-communicating oral interface 318 for negative pressure mucus clearance, permits automated mucus clearance of a sleeping, sedated, or otherwise uncooperative patient. The patient does not have to open his or her mouth to achieve mucus clearance because the mouthpiece forms an airtight seal and connects the negative pressure mucus clearance portion 114 of the medical device 500 with the patient's airway. The lack of fluid communication of the mask 514 and oral interface 318 (except perhaps the theoretical possibility that some small quantity of clean gas from the ventilation portion could mix within the patient with gas removed from the patient by the mucus clearance portion) and the separation of the positive pressure ventilation portion of the device 112 from the negative pressure mucus clearance portion of the device 114 prevent contaminated respiratory secretions from being forced into the patient's lungs under positive pressure, reducing the risk of lung infection.

While various aspects and concepts of the invention are described and illustrated herein as embodied in combination in the exemplary embodiments, these various aspects and concepts may be realized in many alternative embodiments, either individually or in various combinations and sub-combinations thereof. Unless expressly excluded herein all such combinations and sub-combinations are intended to be within the scope of the present invention. Still further, while various alternative embodiments as to the various aspects and features of the invention, such as alternative materials, structures, configurations, methods, devices, software, hardware, control logic and so on may be described herein, such descriptions are not intended to be a complete or exhaustive list of available alternative embodiments, whether presently known or identified herein as conventional or standard or later developed. Those skilled in the art may readily adopt one or more of the aspects, concepts or features of the invention into additional embodiments within the scope of the present invention even if such embodiments are not expressly disclosed herein. Additionally, even though some features, concepts or aspects of the invention may be described herein as being a preferred arrangement or method, such description is not intended to suggest that such feature is required or necessary unless expressly so stated. Still further, exemplary or representative values and ranges may be included to assist in understanding the present invention however, such values and ranges are not to be construed in a limiting sense and are intended to be critical values or ranges only if so expressly stated.

I claim:

1. A medical device for combination lung ventilation and mucus clearance of a patient, comprising:
   a pressure generation source that provides both positive pressure gas flow for lung ventilation and negative pressure suction for mucus clearance, wherein the pressure generation source comprises at least one outlet for the positive pressure gas flow and at least one inlet for the negative pressure suction;
   a ventilation portion for providing positive pressure gas flow to the patient via the nose comprising a nasal interface and a flow channel having a first end and a second end, wherein the first end of the flow channel is in fluid communication with the outlet of the pressure generation source and the second end of the flow channel is in fluid communication with the nasal interface, wherein the ventilation portion includes a pair of ventilation valves, one near the first end of the flow channel adjacent the outlet and the other near the second end of the flow channel adjacent the nasal interface; and
   a mucus clearance portion for providing negative pressure suction to the patient via the mouth comprising a mouth interface and a suction channel having a first end and a second end, wherein the first end of the suction channel is in fluid communication with the inlet of the pressure generation source and the second end of the suction channel is in fluid communication with the mouth interface, wherein the mucus clearance portion includes a pair of suction valves, one near the first end of the suction channel adjacent the inlet and the other near the second end of the suction channel adjacent the mouth interface;
   a control unit for operating the pair of ventilation valves and the pair of suction valves;
   wherein the mucus clearance portion is completely separated from the ventilation portion such that the medical device is capable of maintaining positive pressure lung ventilation via the nasal interface while the mouth interface of the mucus clearance portion of the device is removed from the patient; wherein the pair of ventilation valves are closed by the control unit during use of the mucus clearance portion to provide negative pressure suction to the patient; and wherein the pair of suction valves are closed by the control unit during use of the ventilation portion to provide positive pressure gas flow to the patient, wherein the mucus clearance portion includes a mucus collection receptacle in communication with the suction channel.

2. The medical device of claim 1, wherein the medical device is configured to be used as at least one of a standalone lung ventilation system and a standalone mucus clearance system.

3. The medical device of claim 1, wherein the medical device provides negative pressure suction to the patient via the mouth without removal of the ventilation portion from the patient.

4. The medical device of claim 1, wherein the positive pressure lung ventilation and negative pressure mucus clearance of the patient are provided to the patient without removal of either of the nasal interface or mouth interface from the patient.

5. The medical device of claim 1, wherein the medical device cycles between providing positive pressure lung ventilation and negative pressure mucus clearance of the patient without removal of either of the ventilation portion or the mucus clearance portion from the patient.

6. The medical device of claim 1, wherein in a first configuration the medical device permits the patient's mouth to be free during positive pressure lung ventilation such that the patient can speak, eat, and drink and negative pressure mucus clearance is accomplished intermittently and on demand; and wherein in a second configuration the medical device provides positive pressure lung ventilation and automated negative pressure mucus clearance and permits mucus clearance of a patient that cannot open his or her mouth on command.

7. The medical device of claim 6, wherein the automated negative pressure mucus clearance is accomplished via a timer that initiates negative pressure suction to the patient.

8. The medical device of claim 1, wherein the nasal interface comprises a set of nasal prongs that form a substantially airtight seal with the patient's nasal passages.

9. The medical device of claim 1, wherein the nasal interface comprises a nasal only mask that forms a substantially airtight seal with the patient's nasal passages and has at least one adjustable strap.

10. The medical device of claim 1, wherein the mouth interface comprises a mouthpiece that forms a substantially airtight seal with the patient's mouth comprising a soft outer portion and a hard inner portion having an opening in fluid communication with the suction channel.

11. The medical device of claim 10, wherein the inner portion of the mouthpiece is configured to extend past the teeth of the patient, over at least the tip of the patient's tongue, and into the oral cavity or oropharynx of the patient such that the opening of the inner portion is in fluid communication with the patient's airway to effect respiratory secretion removal from the patient.

12. The medical device of claim 10, wherein the outer portion of the mouthpiece comprises a convex outer surface and a concave inner surface and is configured to be positioned between the inner surface of the patient's lips and the outer surface of the patient's gums to form a substantially airtight seal with the patient's mouth; and wherein the opening at the end of the inner portion of the mouthpiece extends past the patient's teeth, passes over at least the tip of the patient's tongue, and ends in the patient's oral cavity or oropharynx about 1 to 7 cm past the teeth of the patient.

13. The medical device of claim 1, wherein the nasal interface comprises a nasal only mask having at least one adjustable strap and the mouth interface comprises a mouthpiece configured to extend into the oral cavity or oropharynx of the patient.

14. The medical device of claim 1 further comprising a nasal-oral patient interface configured to simultaneously hold the nasal interface in substantially airtight communication with the patient's nasal passages and the mouth interface in substantially airtight communication with the patient's mouth.

15. The medical device of claim 14, wherein the nasal interface and the mouth interface are removably attached to the nasal-oral patient interface.

16. The medical device of claim 14, wherein the nasal interface comprises a set of nasal prongs and the mouth interface comprises a mouthpiece configured to extend into the oral cavity or oropharynx of the patient.

17. The medical device of claim 16, wherein the mouthpiece comprises a soft outer portion and an inner portion having an opening in fluid communication with the suction channel, and wherein the mouthpiece comprises a convex outer surface and a concave inner surface and is configured to be positioned between the inner surface of the patient's lips and the outer surface of the patient's gums to form a substantially airtight seal with the patient's mouth; wherein the inner portion is made from a material of sufficient rigidity such that it may be held between the patient's teeth without collapsing and sufficient rigidity that the conduit between the opening and the suction channel does not collapse during use; and wherein the inner portion of the mouthpiece extends past the patient's teeth, passes over at least the tip of the patient's tongue, and ends in the patient's oral cavity or oropharynx about 1 to 7 cm past the teeth of the patient such that the opening of the inner portion is in fluid communication with the patient's airway to effect respiratory secretion removal from the patient.

18. The medical device of claim 14, wherein the nasal-oral patient interface comprises an inlet connected to the nasal interface through which air is forced into the nose for positive pressure lung ventilation and an outlet connected to the mouth interface through which mucus is suctioned out of the airway of the patient via negative pressure suction applied to the mouth; and no fluid communication exists between the inlet and the outlet of the nasal-oral patient interface.

19. The medical device of claim 1 wherein at least one of the mouth interface and suction channel is removably attached to at least one of an adjustable bracket and a handle such that the patient can insert the mouth interface into his or her mouth without using his or her hands.

20. The medical device of claim 1 further comprising a switch that initiates negative pressure suction and configured to signal opening of the pair of suction valves.

21. The medical device of claim 1, wherein the negative pressure suction is initiated intermittently using an adjustable timer.

22. The medical device of claim 1, wherein the medical device is battery powered to permit portability of the medical device.

23. The medical device of claim 1 wherein the nasal interface comprises a mask having at least one adjustable strap to hold the mask in substantially airtight communication with at least the patient's nasal passages, and wherein the mask is configured to hold the mouth interface in substantially airtight communication with the patient's mouth.

24. The medical device of claim 1 further comprising a control unit configured to provide mucus clearance treatment by first delivering a deep breath of positive pressure gas to the patient via the ventilation portion of the medical device followed by negative pressure suction to the patient via the mucus clearance portion of the medical device.

25. The medical device of claim 1 further comprising a preprogrammed processor programmed to provide a series of deep breaths of positive pressure gas to the patient via the patient's nose, each deep breath being followed by negative pressure suction to the patient via the patient's mouth.

26. The medical device of claim 1 further comprising a control unit configured to operate at least one of the pressure generation source and the pair of ventilation valves to control the positive pressure gas flow to the patient via the patient's nose and at least one of the pressure generation source and the pair of suction valves to control the negative pressure suction to the patient via the patient's mouth.

27. The medical device of claim 26, wherein the control unit comprises a preprogrammed processor programmed to coordinate at least one of the positive pressure and negative pressure cycling of the pressure generation source and the sequential or concurrent operation of the pair of ventilation valves and the pair of suction valves.

28. The medical device of claim 1 further comprising a preprogrammed processor programmed to control the pressure and flow characteristics of the negative pressure suction provided to the patient via the patient's mouth.

29. The medical device of claim 1 further comprising a preprogrammed processor programmed to control the pressure and flow characteristics of the positive pressure gas flow provided to the patient via the patient's nose.

30. A medical device for combination lung ventilation and mucus clearance of a patient, comprising:
- a pressure generation source that provides both positive pressure gas flow for lung ventilation and negative pressure suction for mucus clearance, wherein the pressure generation source comprises at least one outlet for the positive pressure gas flow and at least one inlet for the negative pressure suction;
- a ventilation portion for providing positive pressure gas flow to the patient via the nose comprising:
  - a nasal only mask that forms a substantially airtight seal with the patient's nasal passages and has at least one adjustable strap;
  - a flow channel having a first end and a second end, wherein the first end of the flow channel is in fluid communication with the outlet of the pressure generation source and the second end of the flow channel is in fluid communication with the nasal only mask; and
  - a pair of ventilation valves, one near the first end of the flow channel adjacent the outlet and the other near the second end of the flow channel adjacent the nasal only mask; and
- a mucus clearance portion for providing negative pressure suction to the patient via the mouth comprising:
  - a mouthpiece that forms a substantially airtight seal with the patient's mouth;
  - a suction channel having a first end and a second end, wherein the first end of the suction channel is in fluid communication with the inlet of the pressure generation source and the second end of the suction channel is in fluid communication with the mouthpiece; and
  - a pair of suction valves, one near the first end of the suction channel adjacent the inlet and the other near the second end of the suction channel adjacent the mouthpiece;
- a control unit for operating the pair of ventilation valves and the pair of suction valves;
- wherein the mouthpiece further comprises a soft outer portion and a hard inner portion having an opening in fluid communication with the suction channel, wherein the outer portion of the mouthpiece comprises a convex outer surface and a concave inner surface and is configured to be positioned between the inner surface of the patient's lips and the outer surface of the patient's gums to form a substantially airtight seal with the patient's mouth, and wherein the inner portion of the mouthpiece extends past the patient's teeth, passes on top of at least the tip of the patient's tongue, and ends in the patient's oral cavity or oropharynx such that the opening of the inner portion is in fluid communication with the patient's airway to effect respiratory secretion removal from the patient; and
- wherein the mucus clearance portion is completely separated from the ventilation portion such that the medical device is capable of maintaining positive pressure lung ventilation via the nasal interface with the mouth interface of the mucus clearance portion of the device removed from the patient;
- wherein the medical device provides negative pressure suction to the patient via the mouth without removal of the ventilation portion from the patient; and
- wherein the medical device provides positive pressure lung ventilation and negative pressure mucus clearance of the patient without removal of either of the ventilation portion or the mucus clearance portion from the patient;
- wherein the pair of ventilation valves are closed by the control unit during use of the mucus clearance portion to provide negative pressure suction to the patient; and
- wherein the pair of suction valves are closed by the control unit during use of the ventilation portion to provide positive pressure gas flow to the patient, wherein the mucus clearance portion includes a mucus collection receptacle in communication with the suction channel.

31. A method comprising the steps of:
- providing a nasal interface and a separate mouth interface having a soft outer portion and an inner portion having an opening, wherein the inner portion is made from a material of sufficient rigidity such that it may be held between a person's teeth without collapsing and sufficient rigidity that a conduit within the inner portion does not collapse during use;
- positioning the nasal interface in substantially airtight fluid communication with a person's nasal passages; and
- inserting the mouth interface in the person's mouth, wherein the outer portion of the mouth interface comprises a convex outer surface and a concave inner surface and is configured to be positioned between the inner surface of the person's lips and the outer surface of the person's gums to form a substantially airtight seal with the person's mouth, and wherein the inner portion of mouth interface extends past the person's teeth, passes over at least the tip of the person's tongue, and ends in the person's oral cavity or oropharynx such that the opening of the inner portion is in fluid communication with the person's airway; and
- wherein the nasal interface and the mouth interface are separate and not in fluid communication;
- providing a pressure generation source that supplies both positive pressure gas flow and negative pressure suction, wherein the pressure generation source comprises at least one outlet for positive pressure gas flow and at least one inlet for negative pressure suction;

connecting a first end of a flow channel to the outlet of the pressure generation source and a second end of the flow channel to the nasal interface;

connecting a first end of a suction channel to the inlet of the pressure generation source and a second end of the suction channel to the mouth interface; wherein the flow channel and the suction channel are separate and not in fluid communication;

providing a pair of ventilation valves, one near a first end of a flow channel adjacent the outlet and the other near the second end of the flow channel adjacent the nasal interface;

providing a pair of suction valves, one near the first end of the suction channel adjacent the inlet and the other near the second end of the suction channel adjacent the mouth interface, wherein a mucus collection receptacle is in communication with the suction channel at a position between the pair of suction valves, wherein the communication between the suction channel and the mucus collection receptacle is via a single conduit that taps into the suction channel such that a T-arrangement is formed;

providing a control unit for operating the pair of ventilation valves and the pair of suction valves and operating the control unit to cause closing the pair of ventilation valves during use of the mucus clearance portion to provide negative pressure suction to the patient; and closing the pair of suction valves during use of the ventilation portion to provide positive pressure gas flow to the patient.

32. The method of claim 31, wherein the nasal interface comprises a nasal mask and further comprising securing the nasal mask to the person using adjustable straps.

33. The method of claim 31 further comprising securing a nasal-oral patient interface to the person to simultaneously hold the nasal interface in fluid communication with the person's nasal passages and the mouth interface in communication with the person's mouth.

34. The method of claim 31, wherein the nasal interface comprises a set of nasal prongs.

35. A method of combination lung ventilation and mucus clearance of a patient, comprising the steps of:

providing a positive pressure flow of gas to the lungs of the patient via a first interface in substantially airtight fluid communication with the patient's nasal passages; and providing a negative pressure suction to the airway of the patient via a second interface in substantially airtight fluid communication with the patient's mouth, providing a pressure generation source that supplies both the positive pressure gas flow and the negative pressure suction, wherein the pressure generation source comprises at least one outlet for positive pressure gas flow and at least one inlet for negative pressure suction;

connecting a first end of a flow channel to the outlet of the pressure generation source and a second end of the flow channel to the first interface;

connecting a first end of a suction channel to the inlet of the pressure generation source and a second end of the suction channel to the second interface; wherein the flow channel and the suction channel are separate and not in fluid communication;

providing a pair of ventilation valves, one near a first end of a flow channel adjacent the outlet and the other near the second end of the flow channel adjacent the firstl first interface;

providing a pair of suction valves, one near the first end of the suction channel adjacent the inlet and the other near the second end of the suction channel adjacent the second interface, wherein a mucus collection receptacle is in communication with the suction channel at a position between the pair of suction valves, wherein the communication between the suction channel and the mucus collection receptacle is via a single conduit that taps into the suction channel such that a T-arrangement is formed;

providing a control unit for operating the pair of ventilation valves and the pair of suction valves and operating the control unit to cause closing the pair of ventilation valves during provision of the negative pressure suction to the patient; and closing the pair of suction valves during provision of the positive pressure gas flow to the patient;

wherein positive pressure lung ventilation and negative pressure suction are provided without removal of the first interface or the second interface from the patient, and wherein the first interface is separate from the second interface such that the interfaces are not in fluid communication.

36. The method of claim 35, wherein negative pressure suction is provided to the patient intermittently and on demand and the second interface is removably attached to at least one of an adjustable bracket and a handle to hold the second interface in proximity to the patient.

37. The method of claim 35, wherein negative pressure suction is automated using an adjustable timer and a patient interface is configured to simultaneously hold the first interface in substantially airtight fluid communication with the patient's nasal passages and the second interface in substantially airtight fluid communication with the patient's mouth.

38. The method of claim 35, wherein the second interface comprises a soft outer portion and an inner portion having an opening; and wherein the outer portion of the second interface comprises a convex outer surface and a concave inner surface and is configured to be positioned between the inner surface of the patient's lips and the outer surface of the patient's gums to form a substantially airtight seal with the patient's mouth; wherein the inner portion is made from a material of sufficient rigidity such that it may be held between the patient's teeth without collapsing and sufficient rigidity that the conduit between the opening and the suction channel does not collapse during use; and wherein the inner portion of second interface extends past the patient's teeth, passes on top of the patient's tongue, and ends in the patient's oral cavity or oropharynx such that the opening of the inner portion is in fluid communication with the patient's airway to effect respiratory secretion removal from the patient.

39. The method of claim 35 further comprising providing a deep breath of positive pressure gas to the lungs of the patient via the first interface followed by negative pressure suction to the airway of the patient via the second interface.

40. The method of claim 35 further comprising providing a series of deep breaths of positive pressure gas to the lungs of the patient via the first interface, each deep breath being followed by negative pressure suction to the airway of the patient via the second interface.

* * * * *